United States Patent
Kreek et al.

(10) Patent No.: US 7,033,759 B2
(45) Date of Patent: Apr. 25, 2006

(54) VARIANTS OF THE HUMAN KAPPA OPIOID RECEPTOR GENE

(75) Inventors: Mary Jeanne Kreek, New York, NY (US); Vadim Yuferov, New York, NY (US); Karl Steven LaForge, New York, NY (US)

(73) Assignee: The Rockfeller University, New York, NY (US)

( * ) Notice: Subject to any disclaimer, the term of this patent is extended or adjusted under 35 U.S.C. 154(b) by 8 days.

(21) Appl. No.: 09/904,584

(22) Filed: Jul. 13, 2001

(65) Prior Publication Data

US 2004/0097704 A1 May 20, 2004

Related U.S. Application Data

(60) Provisional application No. 60/218,300, filed on Jul. 14, 2000.

(51) Int. Cl.
*C12Q 1/68* (2006.01)
*C07H 21/04* (2006.01)

(52) U.S. Cl. .................. 435/6; 435/69.1; 435/91.2; 435/252.3; 435/320.1; 536/23.5; 536/24.33

(58) Field of Classification Search ............ 435/6, 435/69.1, 91.2, 252.3, 320.1; 536/23.5, 24.33
See application file for complete search history.

(56) References Cited

U.S. PATENT DOCUMENTS 6,096,513 A * 8/2000 Bell et al. ................ 435/69.1

OTHER PUBLICATIONS pcDNA3 Vector Data from Invitrogen Life Techologies, accessed at http://www.invitrogen.com (Oct. 7, 2004).*
Wells, J.A. (1990). Additivity of mutational effects in proteins. Biochemistry 29:8509–8517.*
Ngo et al. (1990). Computational complexity, protein structure prediction, and the Levinthal paradox. In Merz and Le Grand (Eds.) The Protein Folding Problem and Tertiary Structure Prediction. Birkhauser:Boston.*
Waldhoer et al. (2004). Opioid receptors. Annual Review of Biochemistry 73:953–990.*
Mansson, Erik et al. Biochem Biophys Research Comm vol. 202: pp. 1431–1437 (1994).
Simonin, Frederic et al. Proc. Natl. Acad. Sci USA vol. 92 pp. 7006–7010 (1995).
Zhu, Jinmin et al. Life Sciences vol. 56:(No. 9) pp. 201–207 (1995).
Grandy, D.K. GenBank Accession No. U16860 (1994).
Yasuda, K. et al. GenBank Accession No. L26079 (1995).
Simonin, F. et al. GenBank Accession No. U17298 (1995).

* cited by examiner

*Primary Examiner*—Robert S. Landsman
*Assistant Examiner*—Jon M. Lockard
(74) *Attorney, Agent, or Firm*—Klauber & Jackson

(57) ABSTRACT

Provided herein are variant alleles of a gene encoding a kappa opioid receptor, along with cloning vectors for replicating such variant alleles, and expressing vectors for expressing the variant alleles to produce variant kappa opioid receptors.

12 Claims, No Drawings

VARIANTS OF THE HUMAN KAPPA OPIOID RECEPTOR GENE

CROSS-REFERENCE TO RELATED APPLICATION

Priority 35 U.S.C. § 119(e) is claimed to U.S. provisional application Ser. No. 60/218,300, filed Jul. 14, 2000, incorporated herein by reference in its entirety.

GOVERNMENTAL SUPPORT

This invention was made government support under Grant Nos. NIH-NIDA P50-DA05130, NIH-NIDA K05-DA00049, and NIH-NIDA R01-DA12848, awarded by the National Institute of Drug Addiction. The Government has certain rights in the invention.

FIELD OF THE INVENTION

This invention relates generally to alleles of the human kappa opioid receptor gene, polymorphisms thereof, methods of diagnosing various susceptibilities using such alleles and determining treatment for certain diseases based upon the presence of specific alleles, and various diseases or disorders related thereto.

BACKGROUND OF THE INVENTION

Opioid drugs have various effects on perception of pain, consciousness, motor control, mood, autonomic function, and can also induce physical dependence. The endogenous opioid system plays an important role in modulating endocrine, cardiovascular, respiratory, gastrointestinal functions, and immune functions. Opioids, either exogenous or endogenous, exert their actions by binding to specific membrane-associated receptors.

Examples of exogenous opioids presently known include, opium, heroin, morphine, codeine, fentanyl, and methadone, to name only a few. Moreover, a family of over 20 endogenous opioid peptides has been identified, wherein the members possess common structural features, including a positive charge juxtaposed with an aromatic ring that is required for interaction with an opioid receptor. It has been determined that most, if not all the endogenous opioid peptides are derived from the proteolytic processing of three precursor proteins, i.e., pro-opiomelanocortin, proenkephalin, and prodynorphin. In addition, a fourth class of endogenous opioids, the endorphins, has been identified (the gene encoding these proteins has not yet been cloned). In the processing of the endogenous opioid precursor proteins, initial cleavages are made by membrane-bound proteases that cut next to pairs of positively charged amino acid residues, and then trimming reactions produce the final endogenous opioids secreted from cells in vivo. Different cell types contain different processing enzymes so that, for example proopiomelanocortin can be processed into different endogenous peptides by different cells. For example, in the anterior lobe of the pituitary gland, only corticotropin (ACTH), β-lipotropin, and β-endorphin are produced. Both pro-enkephalin and pro-dynorphin are similarly processed by specific enzymes in specific cells to yield multiple opioid peptides.

Pharmacological studies have suggested there are numerous classes of opioid receptors which bind to exogenous and endogenous opioids. These classes differ in their affinity for various opioid ligands and in their cellular and organ distribution. Moreover, although the different classes are believed to serve different physiological functions, there is substantial overlap of function, as well as of distribution.

In particular, there are at least three known types of opioid receptors, mu (μ), delta (δ), and kappa (κ), to which morphine, the enkephalins, and the dynorphins can bind. These three opioid receptor types are the sites of action of opioid ligands producing analgesic effects. However, the type of pain inhibited and the secondary functions vary with each receptor type. The mu receptor is generally regarded as primarily associated with pain relief, and drug or other chemical dependence, i.e., addiction and alcoholism.

One such gene structurally related to the opioid receptor genes is the human kappa opioid (hKOR) receptor gene. The receptor is widely distributed in the CNS and periphery (including immune cells) and plays important and diverse roles in modulation of the endogenous opioid system, nociception, neurotransmitter release (including dopamine, GABA, and serotonin), learning, memory and cognition; cocaine, amphetamine and other stimulants self-administration; behavioral sensitization to cocaine, opiates, alcohol and tobacco; opiate, amphetamine and alcohol withdrawal, physical dependence and tolerance; neuroendocrine function, reproductive function, prolactin regulation, stress responsivity; physiology and pathology of mood and affect; immune function, and gastrointestinal function. See, for example, Simonin F, Valverde O, Smadja C, Slowe S, Kitchen I, Dierich A, Le Meur M, Roques B P, Maldonado R, Kieffer B L, 1998, Disruption of the kappa-opioid receptor gene in mice enchances sensitivity to chemical visceral pain, impaires pharmacological actions of the selective kappa-agonist U-50,488H and attenuates morphine withdrawal, *EMBO J.*, 17: 886–897; Slowe S, Simonin F, Kieffer B, Kitchen I. 1999, Quantitative autoradiography of μ-, δ- and $κ_1$-opioid receptors in k-opioid receptor knockout mice, *Brain research,* 818: 335–345; Heidbreder C A, Schenk S, Partridge B, Shippenberg T S. 1998, Increased responsiveness of mesolimbic and mesostriatal dopamine neurons to cocaine following repeated administration of a selective kappa-opioid receptor agonist, *Synapse,* 30: 255–262; Schenk S, Partridge B, Shippenberg T S. 1999, U69593, a kappa-opioid agonist, decreases cocaine self-administration and decreases cocaine-produced drug-seeking, *Psychopharmacology* (Berl), 144: 339–346; Kreek M J, Schluger J, Borg L, Gunduz M, Ho A. 1999, Dynorphin A1-13 causes elevation of serum levels of prolactin through an opioid receptor mechanism in humans: gender differences and implications for modulation of dopaminergic tone in the treatment of addictions. *JPET,* 288: 260–269; Portenoy R, Caraceni A, Cherny N I, Goldblum R, Ingham J, Inturrisi C E, Johnson J H, Lapin J, Tiseo P J, Kreek M J. 1999, Dynorphin A(1-13) analgesia in opioid-treated patients with chronic pain. *Clin Drug Invest.,* 17: 33–42; Milan M J. 1990, κ-Opioid receptors and analgesia. *TiPS,* 11: 70–76; Mansson E, Bare L, Yang D., 1994, Isolation of human k opioid receptor cDNA from placenta, *Bioch Biophys Res Communications,* 202, 1431–1437; Simonin F, Gaveriaux-Ruff C, Befort K, Matthes H, Iannes B, Micheletti G, Mattei M-G, Charron G, Bloch B, Kieffer B., 1995, k-Opioid receptor in humans: cDNA and genomic cloning, chromosomal assignment, functional expression, pharmacology, and expression pattern in the central nervous system, *Proc Natl Acad Sci USA,* 92, 7006–7010; Zhu J, Chen C, Xue J-C, Kunapuli S, DeRiel J K, Liu-Chen L-Y., 1995, Cloning of a human k opioid receptor from the brain, *Life Sciences,* 56, 201–207; Grandy D K., 1994, Mapping of the human kappa opioid receptor gene to chromosome 8q11.2-q12: no evidence for multiple kappa opioid receptor genes (partial sequence of exon II and downstream intron). GenBank entry, Accession # U16860; and Yasuda K, Espinosa R, Takeda J, Le Beau M M, Bell G I., 1995, Localization of kappa opioid receptor gene to human chromosome band 8q11.2 (sequence of exon II), GenBank entry, Accession # L26079. Three GenBank entries for hKOR are U17298, NM_000912, and L37362. These as well as all publications cited herein are incorporated herein by reference in their entireties.

It is toward the identification of both the wild-type human kappa opioid receptor gene as well as alleles other than the most common or wild-type allele of the human kappa opioid receptor gene, polymorphisms therein, and combinations of such polymorphisms that can be used as genetic markers to map the locus of the human kappa opioid receptor gene in the genome, and additionally to correlate such polymorphisms of the human kappa opioid receptor gene with susceptibility of a subject to any of the various physiological functions, conditions and diseases mentioned hereinabove in which the kappa opioid receptor gene plays a role, including but not limited to determine a subject's increased or decreased susceptibility to addictive diseases, susceptibility to pain and response to analgesics, physiological responses related to the endogenous opioid system, nociception, neurotransmitter release (including dopamine, GABA, and serotonin), learning, memory and cognition; cocaine, amphetamine and other stimulants self-administration; behavioral sensitization to cocaine, opiates, alcohol and tobacco; opiate, amphetamine and alcohol withdrawal, physical dependence and tolerance; neuroendocrine function, reproductive function, prolactin regulation, stress responsivity; physiology and pathology of mood and affect; immune function, and gastrointestinal function; among other uses, that the present invention is directed.

The citation of any reference herein should not be construed as an admission that such reference is available as "Prior Art" to the instant application.

SUMMARY OF THE INVENTION

There is provided, in accordance with the present invention, heretofore unknown single-nucleotide polymorphisms (SNPs) of the human kappa opioid receptor gene, and their use in mapping the locus of the human kappa opioid receptor gene; determining susceptibility to addictive diseases; determining susceptibility to pain; determining a therapeutically effective amount of pain reliever to administer to a subject suffering from pain; diagnosing a disease or disorder in a subject related to a physiological response, condition or disorder such as but not limited to the endogenous opioid system, nociception, neurotransmitter release (including dopamine, GABA, and serotonin), learning, memory and cognition; cocaine, amphetamine and other stimulants self-administration; behavioral sensitization to cocaine, opiates, alcohol and tobacco; opiate, amphetamine and alcohol withdrawal, physical dependence and tolerance; neuroendocrine function, reproductive function, prolactin regulation, stress responsivity; physiology and pathology of mood and affect; immune function, and gastrointestinal function; and selecting an appropriate therapeutic agent and a therapeutically effective amount of such an agent to administer to a subject suffering from an aforementioned disease or disorder. One or more of the polymorphisms of the invention may be employed as such; and an individual may have one or more of the polymorphisms. Moreover, the polymorphisms individually and in combination may be present homozygously or heterozygously.

The single-nucleotide polymorphisms identified herein are present in exon III of the hKOR gene: C852T (SEQ ID No:2), present in transmembrane region (TM) VI; C948T (SEQ ID No:3), present in TM VII; and C1008T (SEQ ID No:4), present in the C-terminal region of exon III.

In addition, by comparing the published HKOR GenBank sequences mentioned above with the sequences of the KOR of numerous subjects in the study described hereinbelow, the present inventors have identified the most common, or wild-type, allele of hKOR (SEQ ID No:1) and determined that variations therein which are present in the aforementioned GenBank sequences are indeed single nucleotide polymorphisms (SNPs) of hKOR, in particular, those in NM_000912 as compared with U17298 or L37362. These polymorphisms are G36T (SEQ ID No:5), present in the N-terminal portion of exon I of HKOR; and in exon III, the polymorphisms A843G (SEQ ID No:6), present in TM VI; and C846T (SEQ ID No:7), present in TM VI. All of these SNPs are silent, i.e., they do not alter the predicted amino acid sequence of the encoded receptor protein.

Thus, in summary, the polymorphisms identified herein in the human kappa opioid receptor are C852T (SEQ ID No:2), C948T (SEQ ID No:3), C1008T (SEQ ID No:4), G36T (SEQ ID No:5), A843G (SEQ ID No:6), and C846T (SEQ ID No:7). The wild-type or most common allele has been identified herein as that depicted in SEQ ID No:1.

The present invention extends to DNA sequences of heretofore unknown isolated nucleic acid molecules which encode human kappa opioid receptors, wherein the DNA sequences include any combination of the aforementioned known polymorphisms.

The present invention further extends to diagnostic methods to determine a subject's increased or decreased susceptibility to addictive diseases. With the results of such methods, targeted prevention methods, early therapeutic intervention, and improved chronic treatment to opioid addiction are set forth herein and encompassed by the present invention. In addition, attending medical professionals armed with the results of such diagnostic methods can determine whether administration of opioid analgesics is appropriate or whether non-opioid derived analgesics should be administered to the subject. Furthermore, appropriate choice and type of analgesic to treat a subject's pain can be made. Such determination may be made by identification of any individual or any combination of the above-mentioned polymorphisms, using such non-limiting methods as DNA sequencing, differential hybridization to biological chip arrays such as an oligonucleotide gelpad microchip, or single nucleotide extension (SNE) on chip arrays such as on oligonucleotide gelpad microchips.

Broadly the present invention extends to an isolated variant allele of a human kappa opioid receptor gene which can serve as a genetic marker, wherein the predominant or "most common" allele of a human kappa opioid receptor gene found in the population comprises a DNA sequence of SEQ ID NO:1, and a variant allele of the present invention comprises a DNA sequence having a variation in SEQ ID NO:1, wherein the variation comprises G36T, A843G, C846T, C852T, C948T, C1008T, or any combination thereof.

Furthermore, the present invention extends to an isolated variant allele of a human kappa opioid receptor gene as set forth above, which is detectably labeled. Numerous detectable labels have applications in the present invention, such as radioactive elements, chemicals which fluoresces, or enzymes, to name only a few.

The present invention further extends to an isolated nucleic acid molecule selectively hybridizable to an isolated variant allele of the human kappa opioid receptor gene, wherein the predominant or "most common" allele of a human kappa opioid receptor gene found in the population comprises a DNA sequence of SEQ ID NO:1, and a variant allele of the present invention comprises a DNA sequence having a variation in SEQ ID NO:1, wherein the variation comprises G36T, A843G, C846T, C852T, C948T, C1008T, or any combination thereof.

Moreover, the present invention extends to an isolated nucleic acid molecule selectively hybridizable to an isolated variant allele of the human kappa opioid receptor gene, wherein the predominant or "most common" allele of a human kappa opioid receptor gene found in the population comprises a DNA sequence of SEQ ID NO:1, and a variant allele of the present invention comprises a DNA sequence having a variation in SEQ ID NO:1, wherein the variation comprises G-46A, G36T, A843G, C846T, C852T, C948T, C1008T, or any combination thereof, wherein the isolated nucleic acid molecule is detectably labeled. Examples of detectable labels that have applications in this embodiment of the present invention are described above.

In addition, the present invention extends to cloning vectors that can be used to clone copies of a variant alleles of a human kappa opioid receptor gene of the present invention. For example, the present invention extends to a cloning vector comprising an isolated variant allele of a human kappa opioid receptor gene and an origin of replication, wherein the predominant or "most common" allele of a human kappa opioid receptor gene found in the population comprises a DNA sequence of SEQ ID NO:1, and a variant allele of the present invention comprises a DNA sequence having a variation in SEQ ID NO:1, wherein the variation comprises G36T, A843 G, C846T, C852T, C948T, C1008T, or any combination thereof.

In another embodiment, the present invention extends to a cloning vector comprising an isolated nucleic acid molecule selectively hybridizable to an isolated variant allele of a human kappa opioid receptor gene, and an origin of replication, wherein the predominant or "most common" allele of a human kappa opioid receptor gene found in the population comprises a DNA sequence of SEQ ID NO:1, and a variant allele of the present invention comprises a DNA sequence having a variation in SEQ ID NO:1, wherein the variation comprises G36T, A843G, C846T, C852T, C948T, or C1008T, or any combination thereof.

Numerous cloning vectors have applications in the present invention. For example, a cloning vector having applications in the present invention includes *E. coli*, bacteriophages such as lambda derivatives, plasmids such as pBR322 derivatives, and pUC plasmid derivatives such as pGEX vectors or pmal-c or pFLAG, to name only a few.

Naturally, the present invention extends to expression vectors comprising an isolated variant allele a human kappa opioid receptor gene operatively associated with a promoter, wherein the predominant or "most common" allele of a human kappa opioid receptor gene found in the population comprises a DNA sequence of SEQ ID NO:1, and a variant allele of the present invention comprises a DNA sequence having a variation in SEQ ID NO:1, wherein the variation comprises G36T, A843G, C846T, C852T, C948T, or C1008T, or any combination thereof.

Furthermore, the present invention extends to an expression vector comprising an isolated nucleic acid molecule selectively hybridizable to an isolated variant allele a human kappa opioid receptor gene, wherein the isolated nucleic acid molecule is operatively associated with a promoter. As set forth above, the predominant or "most common" allele of a human kappa opioid receptor gene found in the population comprises a DNA sequence of SEQ ID NO:1, and a variant allele of the present invention comprises a DNA sequence having a variation in SEQ ID NO:1, wherein the variation comprises G36T, A843G, C846T, C852T, C948T, or C1008T, or any combination thereof.

Numerous promoters have applications in an expression vector of the present invention, including but not limited to immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the trp system, the TAC system, the TRC system, the major operator and promoter regions of phage lambda, control regions of fd coat protein, 3-phosphoglycerate kinase promoter, acid phosphatase promoter, or promoters of yeast a mating factor, to name only a few.

In addition, the present invention extends to a unicellular host transformed or transfected with an expression vector of the present invention. Examples of hosts which can be transformed or transfected with an expression vector of the present invention, and have applications in the present invention, include, but are not limited to, *E. coli, Pseudomonas, Bacillus, Streptomyces*, yeast, CHO, R1.1, B-W, L-M, COS1, COS7, BSC1, BSC40, BMT10 or Sf9 cells.

The invention further extends to altered expression of the wild-type kappa opioid gene product, and means for detecting the altered expression, as a consequence of the presence of any one or any combination of the polymorphisms G36T, A843G, C846T, C852T, C948T, or C1008T.

Accordingly, the present invention extends to a method for determining a susceptibility in a subject to at least one disease, comprising the steps of removing a bodily sample comprising a first and second allele of a human kappa opioid receptor gene from the subject, and determining whether the first allele comprises a human kappa opioid receptor gene comprising a DNA sequence having at least one variation in SEQ ID NO:1, wherein the variation comprises G36T, A843G, C846T, C852T, C948T, or C1008T.

It The present of at least one of these variations in the human kappa opioid receptor gene of the first allele is expected to be indicative of the subject's susceptibility to at least one disease relative to the susceptibility of a standard, wherein the standard comprises a first allele comprising a human kappa opioid receptor gene having a DNA sequence of SEQ ID NO:1.

Another embodiment of the method for determining a susceptibility in the subject to at least one disease, as described above, comprises the further step of determining whether the second allele of the bodily sample of the subject comprises a human kappa opioid receptor gene comprising a DNA sequence having at least one variation in SEQ ID NO:1, wherein the variations comprise G36T, A843G, C846T, C852T, C948T, or C1008T.

Furthermore, the present invention extends to a method for determining a susceptibility to pain in a subject relative to susceptibility to pain in a standard, comprising the steps of removing a bodily sample comprising a first and second allele of a human kappa opioid receptor gene from the subject, and determining whether the first allele comprises a human kappa opioid receptor gene comprising a DNA sequence having at least one variation in SEQ ID NO:1, wherein the variation comprises one or more of the polymorphisms G36T, A843G, C846T, C852T, C948T, or C1008T. The presence of at least one variation in the human kappa opioid receptor gene of the first allele is expected to be indicative of a decreased or increased susceptibility to pain in the subject relative to susceptibility to pain in the standard, wherein the first allele of the standard comprises a human kappa opioid receptor gene comprising a DNA sequence of SEQ ID NO:1.

Moreover, a method for determining a susceptibility to pain in a subject may further comprise the step of determining whether the second allele comprises a human kappa opioid receptor gene comprising a DNA sequence having at least one variation in SEQ ID NO:1, wherein the variation comprises one or more of the polymorphisms G36T, A843G, C846T, C852T, C948T, or C1008T. The presence of the at least one variation in the human kappa opioid receptor gene of the second allele of the bodily sample from the subject is expected to be indicative of an increased or decreased susceptibility to pain in the subject relative to the susceptibility to pain in the standard, wherein the second allele in the standard comprises a human kappa opioid receptor gene comprising a DNA sequence of SEQ ID NO:1.

Consequently, the present invention extends to a method for determining a therapeutically effective amount of pain reliever to administer to a subject in order to induce analgesia in the subject relative to a therapeutically effective amount of the pain reliever to administer to a standard in order to induce analgesia in the standard, wherein the method comprises determining a susceptibility to pain in the subject relative to susceptibility to pain in the standard. The susceptibility of pain in the subject is expected to be indicative of the therapeutically effective amount of the pain reliever to administer to the subject to induce analgesia in the subject relative to the amount of the pain reliever to administer to the standard to induce analgesia in the standard.

Hence, the present invention extends to a method for determining a therapeutically effective amount of pain reliever to administer to a subject in order to induce analgesia in the subject relative to a therapeutically effective amount of the pain reliever to administer to a standard in order to induce analgesia in the standard wherein the method comprises the steps of removing a bodily sample comprising a first and second allele of a human kappa opioid receptor gene from the subject, and determining whether the first allele comprises a human kappa opioid receptor gene comprising a DNA sequence having at least one variation in SEQ ID NO:1, wherein the at least one variation comprises G36T, A843G, C846T, C852T, C948T, or C1008T. The presence of at least one variation in the human kappa opioid receptor gene of the first allele from the bodily sample is expected to be indicative of the therapeutically effective amount of pain reliever to administer to the subject to induce analgesia in the subject relative to the therapeutically effective amount of pain reliever to administer to the standard to induce analgesia in the standard, wherein the standard comprises a first allele comprising a human kappa opioid receptor gene comprising a DNA sequence of SEQ ID NO:1.

Moreover, the present invention further extends to a method for determining a therapeutically effective amount of pain reliever to administer to a subject in order to induce analgesia in the subject relative to a therapeutically effective amount of pain reliever to administer to a standard to induce analgesia therein, further comprising the steps of removing a bodily sample comprising a first and second allele comprising a human kappa opioid receptor gene from the subject, and determining whether the second allele of the bodily sample comprises a human kappa opioid receptor gene comprising a DNA sequence comprising at least one variation in SEQ ID NO:1, wherein the at least one variation comprises G36T, A843G, C846T, C852T, C948T, or C1008T. The presence of at least one variation in the human kappa opioid receptor gene of the first and/or second allele of the bodily sample is expected to be indicative of the therapeutically effective amount of pain reliever to administer to the subject to induce analgesia therein relative to the amount of pain reliever to administer to a standard to induce analgesia therein, wherein the first and second alleles of the standard comprise a human kappa opioid receptor gene comprising a DNA sequence of SEQ ID NO:1.

Examples of pain relievers having applications in this embodiment of the present invention include, but are not limited to, morphine, codeine, dihydromorphin, meperidine, methadone, fentanyl and its congeners, butorphenol, nalbuphine, LAAM, or propoxyphine, to name only a few.

The present invention further extends to commercial test kits suitable for use by a medical professional to determine whether either or both alleles of a bodily sample taken from a subject comprise a DNA sequence having at least one variation in SEQ ID NO:1, wherein the variation comprises G36T, A843G, C846T, C852T, C948T, or C1008T.

Commercial test kits of the present invention have applications in determining susceptibility of pain in the subject relative to a standard. Such kits can also be used to determine a subject's increased or decreased susceptibility to at least one addictive disease relative to susceptibility to at least one addictive disease in a standard. Also a therapeutically effective amount of pain reliever to administer to the subject in order to induce analgesia in the subject relative to a therapeutically effective amount of pain reliever to administer to a standard to induce analgesia in the standard can be determined. Moreover, a test kit of the present invention has applications in determining a therapeutically effective amount of therapeutic agent for treating at least one physiological response, condition or disease to administer to a subject suffering therefrom, relative to a therapeutically effective amount of therapeutic agent to administer to a standard.

Furthermore, a commercial test kit of the present invention can also be used to determine the presence of an isolated variant allele of a human kappa opioid receptor gene of the present invention in a bodily sample removed from a subject, which can serve as a genetic marker. As explained above, the predominant or "most common" allele of a human kappa opioid receptor gene found in the population comprises a DNA sequence of SEQ ID NO:1. Hence a variant allele comprising a DNA sequence having a variation in SEQ ID NO:1, wherein the variation comprises G36T, A843G, C846T, C852T, C948T, or C1008T, or combinations thereof, can be detected in the bodily sample with a commercial kit of the invention.

Accordingly, a commercial test kit may be prepared for determining the presence of at least one variation in a human kappa opioid receptor gene of either or both alleles in a bodily sample taken from a subject, wherein the commercial test kit comprises:
   a) PCR oligonucleotide primers suitable for detection of an allele comprising a human kappa opioid receptor gene having a DNA sequence with a variation in SEQ ID NO:1;
   b) other reagents; and
   c) directions for use of the kit.

Accordingly, the present invention extends to a commercial test kit having applications set forth above, comprising a predetermined amount of at least one detectably labeled immunochemically reactive component having affinity for a variant human kappa opioid receptor;

(b) other reagents; and (c) directions for use of the kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the human kappa opioid receptor of a bodily sample to a detectable label;

(b) one or more additional immunochemical reagents of which at least one reagent is a ligand or an immobilized ligand, which ligand comprises:

(i) a ligand capable of binding with the labeled component (a);

(ii) a ligand capable of binding with a binding partner of the labeled component (a);

(iii) a ligand capable of binding with at least one of the component(s) to be determined; or (iv) a ligand capable of binding with at least one of the binding partners of at least one of the component(s) to be determined; or (c) directions for the performance of a protocol for the detection and/or determination of one or more components of an immunochemical reaction between the human kappa opioid receptor gene of the present invention and a specific binding partner thereto.

The present invention is also directed to the finding of the most common, or wild-type, human kappa opioid receptor gene sequence, as depicted in SEQ ID No:1.

Accordingly, it is an object of the present invention to provide heretofore unknown variations the DNA sequence of the human kappa opioid receptor gene wherein the variations can be used to map the locus of the human kappa opioid receptor gene.

It is yet another object of the present invention to use heretofore unknown polymorphisms of an allele of the human kappa opioid receptor gene as markers for any kind of disorder related to the human kappa opioid receptor, such as an addictive disease, pain, or markers for genes.

It is another object of the present invention to provide nucleotides, optionally detectably labeled, selectively hybridizable to variant alleles of the human kappa opioid receptor gene disclosed herein, as well as polypeptides produced from the expression of the variant alleles and nucleotides selectively hybridizable thereto under selective hybridization conditions.

It is another object of the present invention to gain insight into a subject's susceptibility to pain. This insight can be used to determine a therapeutically effective dose of pain reliever to administer to the subject to induce analgesia therein relative to the therapeutically effective amount of pain reliever administered to a standard to induce analgesia therein, wherein the standard comprises two alleles of the human kappa opioid receptor gene comprising a DNA sequence of SEQ ID NO:1.

Such information can be used to tailor a regimen for treating a subject suffering from at least one addictive disease, relative to the therapeutically effective amount of therapeutic agent administered to a standard suffering from at least one addictive disease.

It is yet another object of the present invention to provide commercial test kits for attending medical professionals to determine the presence of variant alleles of a human kappa opioid receptor gene in a bodily sample taken from a subject. The results of such testing can then be used to determine the subjects nociception, neurotransmitter release (including dopamine, GABA, noradrenaline, and serotonin), learning, memory and cognition; cocaine, amphetamine and other stimulants self-administration; behavioral sensitization to cocaine, opiates, alcohol and tobacco; opiate, amphetamine and alcohol withdrawal, physical dependence and tolerance; neuroendocrine function, reproductive function, prolactin regulation, stress responsivity; physiology and pathology of mood and affect; immune function, and gastrointestinal function; determining a therapeutically effective amount of pain reliever to administer to the subject in order to induce analgesia, or determining a therapeutically effective amount of therapeutic agent for treating at least one addictive disease to administer to the subject.

It is yet another object of the present invention to provide commercial detecting variant alleles of the human kappa opioid receptor gene or the presence of a variant human kappa opioid receptor in a bodily sample taken from a subject. The results of such tests can then be used to gain incite into a subject's ability to withstand pain, susceptibility to addiction, to diagnose a disease or disorder related to nociception, neurotransmitter release (including dopamine, GABA, noradrenaline, and serotonin), learning, memory and cognition; cocaine, amphetamine and other stimulants self-administration; behavioral sensitization to cocaine, opiates, alcohol and tobacco; opiate, amphetamine and alcohol withdrawal, physical dependence and tolerance; neuroendocrine function, reproductive function, prolactin regulation, stress responsivity; physiology and pathology of mood and affect; immune function, and gastrointestinal function.

These and other aspects of the present invention will be better appreciated by reference to the following drawings and Detailed Description.

DETAILED DESCRIPTION OF THE INVENTION

As explained above, the present invention is based upon Applicants' surprising and unexpected discovery of heretofore unknown single nucleotide polymorphisms (SNPs) in the human kappa opioid receptor (hKOR) gene, along with combinations thereof. Polymorphisms in this gene have not been previously recognized or known. Furthermore, Applicants have identified the most common, or wild-type allele, of the HKOR, SEQ ID No:1, based on sequencing hKOR genes from a large number of individuals, and have identified in one of the previously-known hKOR sequences as a variant thereof, comprising three polymorphisms. In addition, the inventors herein have discovered that more than one polymorphism can be present in either or both alleles of the human kappa opioid receptor gene in a subject.

In addition, the present invention is based upon Applicants' surprising discovery of molecules of heretofore unknown isolated nucleic acid molecules which encode human kappa opioid receptors, wherein the DNA sequences comprise one or more polymorphisms as set forth herein.

Furthermore, the present invention is based upon Applicants' surprising and unexpected discovery that the expression of variant alleles of the human kappa opioid receptor gene comprising a DNA sequence having a variation in SEQ ID NO:1, wherein the variations are C852T (SEQ ID No:2), present in transmembrane region (TM) VI of exon III; C948T (SEQ ID No:3), present in TM VII of exon III; C1008T (SEQ ID No:4), present in the C-terminal region of exon III; G36T (SEQ ID No:5), present in the N-terminal portion of exon I; A843G (SEQ ID No:6), present in TM VI of exon III; and C846T (SEQ ID No:7), present in TM VI of exon III.

The present invention further extends to heretofore unknown polymorphisms of the human kappa opioid receptor gene that can serve as genetic markers to map the locus of the human kappa opioid receptor gene.

As noted above, the human kappa opioid receptor plays important and diverse roles in modulation of the endogenous opioid system, nociception, neurotransmitter release (including dopamine, GABA, and serotonin), learning, memory and cognition; cocaine, amphetamine and other stimulants self-administration; behavioral sensitization to cocaine, opiates, alcohol and tobacco; opiate, amphetamine and alcohol withdrawal, physical dependence and tolerance; neuroendocrine function, reproductive function, prolactin regulation, stress responsivity; physiology and pathology of mood and affect; immune function, and gastrointestinal function. As noted herein, reference to the identification of one or more of the polymorphisms described herein and the relationship to physiological response, conditions, disorders, diseases, pathologies, aberrations, and other variations in normal or pathological states relating to the aforementioned physiologic processes is embraced herein as utilities for which the identification of the polymorphisms may be applied. Moreover, the identification of the polymorphisms, whether heterozygous, homozygous, single or multiple polymorphisms in an individual and the linkage of such single or multiple polymorphisms, homozygous or heterozygous, to susceptibility, propensity, therapeutic potential, and other factors are further embraced herein.

The present invention extends to diagnostic methods to determine a subject's increased or decreased susceptibility to at least one disease, including addictive disease. With the results of such methods, targeted prevention methods, early therapeutic intervention, and improved chronic treatment to opioid addiction are set forth herein and encompassed by the present invention. In addition, attending medical professionals of subjects armed with the results of such diagnostic methods can determine whether administration of opioid analgesics is appropriate or whether non-opioid derived analgesics should be administered to the subject. Also, appropriate choice and type of analgesic can be made in treating a subject's pain.

Methods for determining the presence of the one or more polymorphisms may be made using any of a large variety of methods for identifying altered nucleotides present in a nucleic acid sequence, by way of non-limiting examples as conventional DNA sequencing, differential hybridization to biological chip arrays such as an oligonucleotide gelpad microchip, or single nucleotide extension (SNE) on chip arrays such as on oligonucleotide gelpad microchips. These methods are known to one of skill in the art, and are merely exemplified by the following citations: Khrapko K R, Lysov Y P, Khorlin A, Shick W V, Florentiev V L, Mirzabekov A D. 1989. An oligonucleotide hybridization approach to DNA sequencing. FEBS Lett 256:118–122; Khrapko K R, Lysov Y P, Khorlin A A, Ivanov I B, Yershov G M, Vasilenko S L, Florentiev V, Mirzabekov A D, 1991, A method for DNA sequencing by hybridization with oligonucleotide matrix. J DNA sequencing 1: 375–388; Fodor S P A, Read J L, Pirrung M C, Stryer L, Lu A T, Solas, D, 1991, Light directed, spatially addressable parallel chemical synthesis. Science 251:776–773; Southern E M, Maskos U, Elder J K, 1992, Analyzing and comparing nucleic acid sequences by hybridization to arrays of oligonucleotides: evaluation using experimental models, Genomics 13:1008–1017; Chee M, Yang R, Hubbell E, Berno A, Huang X C, Stern D, Winkler J, Lockhart D J, Morris M S, Fodor S P A. 1996. Accessing genetic information with high-density DNA arrays. Science 274:610–614; Hacia J G, Brody L C, Chee M S, Fodor S P A, Collins F. 1996. Detection of heterozygous mutations in BCRA1 using high density oligonucleotide arrays and two colour florescence analysis. Nature Genet 14:44–447; Yershov G, Barsky V, Belgovskiy A, Kirillov E, Kreindlin E, Ivanov I, Parinov S, Guschin D, Drobishev A, Dubiley S, Mirzabekov A. 1996. DNA Analysis and diagnostics on oligonucleotide microchips. Proc Natl Acad Sci USA 93:4913–4918; Shick V V Lebed Y B, Kryukov G V. 1998. Identification of HLA DQA1 alleles by the oligonucleotide microchip method. Mol Biol 32:697–688. Translated from Molekulyarna Biologiya 32:813–822; Wang D G, Fan J-B, Siao C-J, Berno A, Young P, Sapolsky R, Ghandour G, Perkins N, Winchester E, Spencer J, Kruglyak L, Stein L, Hsie L, Topaloglou T, Hubbell E, Robinson E, Mittmann M, Morris M S, Shen N, Kilburn D, Rioux J, Nusbaum C, Rozen S, Hudson T J, Lipschutz R, Chee M, Lander E S. 1998 Large scale identification, mapping and genotyping of single-nucleotide polymorphisms in the human genome. Science 280:1077–1082; Halushka M K, Fan J -B, Bentley K, Hsie L, Shen N, Weder A, Cooper R, Lipshutz R, Chakravarti A. 1999. Patterns of single-nucleotide polymorphisms in candidate genes for blood pressure homeostasis. Nature Genet 22:239–247; Cargill M, Altschuler D, Ireland J, Sklar P, Ardlie K, Patil N, Lane C R, Lim E P, Kalyanaraman N, Nemesh J, Ziaugra L, Friedland L, Rolfe A, Warrington J, Lipshutz R, Daley G Q, Lander E S. 1999. Characterization of single nucleotide polymorphisms in coding regions of human genes. Nature genet 22; 231–238; Parinov S, Barsky V, Yershov G, Kirillov E, Timofeev E, Belgovskiy A, Mirzabekov A. 1996. DNA sequencing by hybridization to microchip octa- and decanucleotides extended by stacked pentanucleotides. Nucleic Acids Res 24:2998–3004; Guschin D, Yershof G, Zaslavsky A, Gemmell A, Shick V, Proudnikov V, Arenkov P, Mirzabekov A. 1997. Manual manufacturing of oligonucleotide, DNA and protein microchips. Anal Biochem 250:203–211; Drobyshev A, Mologina M. Shik V, Pobedimskaya D, Yershov G, Mirzabekov A. 1997. Sequence analysis by hybridization with oligonucleotide microchip: Identification of b-thalassemia mutations. Gene 188:45–52; Syvänen A-C, Aalto-Setälä K, Harju L, Kontula K, SØderlund H. 1990. A primer-guided nucleotide incorporation assay in the genotyping of apolipoprotein E. Genomics 8:684–692; Pastinen T, Kurg A, Metspalu A, Peltonen L, Syvänen A-C. 1997. Minisequencing: A specific tool for DNA analysis and diagnostics on oligonucleotide arrays. Genome res 7:606–614; Pastinen T, Perola M, Niini P, Terwilliger J, Salomaa V, Vartiainen E, Peltonen L, Syvänen A-C. 1998. Array-based multiplex analysis of candidate gene reveals two independent and additive genetic risk factors for myocardial infarction in the Finnish population. Hum Mol Genet 7:1453–1462; Dubiley S, Kirillov E, Mirzabekov A. 1999. Polymorphism analysis and gene detection by minisequencing on an array of gel-immobilized primers. Nucleic Acids Res 27:e19; and Syvänen A-C. 1999. From gels to chips: "Minisequencing" primer extension analysis of point mutations and single nucleotide polymorphisms. Hum Mutat 13:1–10. Such citations are not intended to be limiting but merely exemplary of the various methods available for detecting one or more of the polymorphisms described herein.

Also, the present invention extends to methods of determining a subject's increased or decreased susceptibility to pain and response to analgesics, and using that information when prescribing analgesics to the subject.

The present invention further extends to variant alleles of the human kappa opioid receptor gene comprising a DNA sequence comprising one or more heretofore unknown polymorphisms, G36T, A843G, C846T, C852T, C948T, or C1008T.

Consequently, an initial aspect of the present invention involves isolation of heretofore unknown variant alleles of the human kappa opioid receptor gene. As used herein, the term "gene" refers to an assembly of nucleotides that encode a polypeptide, and includes cDNA and genomic DNA nucleic acids.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [*IPL Press,* (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. Polynucleotides capable of discriminating between the wild-type and polymorphic alleles of the invention ("selectively hybridizable") may be prepared, and the conditions under which such polynucleotides selectively hybridize with the polymorphisms of the invention, may be achieved following guidance provided in the art, such as described by Conner et al., 1983, *Proc. Nat. Acad. Sci. U.S.A.* 80:278–82; Yershov et al., 1996, *Proc. Nat. Acad. Sci. U.S.A.* 93:4913–18; Drobyshev et al., 1997, *Gene* 188:45–52; and Chee et al., 1996, *Science* 274:610–614. Selectively hybridizable reporting polynucleotides such as molecular beacons are also well known in the art.

For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC.

Hybridization requires that the two nucleic acids contain complementary sequences, although depending on the stringency of the hybridization, mismatches between bases are possible. The appropriate stringency for selectively hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a selectively hybridizable nucleic acid is at least about 10 nucleotides; preferably at least about 20 nucleotides; and more preferably the length is at least about 30 nucleotides; and most preferably 40 nucleotides. As noted above, the skilled artisan will be guided by the teachings in the art on selecting the length of a polynucleotide or nucleic acid sequence, the position(s) of the variant nucleotide(s), and the conditions and instrumentation to selectively identify nucleic acid sequences comprising one or more of the polymorphisms as described herein.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" or "promoter" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A coding sequence is "operatively associated with" a transcriptional and translational control sequences, such as a promoter for example, when RNA polymerase transcribes the coding sequence into mRNA, which in turn is translated into a protein encoding by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to selectively hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to selectively hybridize therewith and thereby form the template for the synthesis of the extension product.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

The phrase "expected to be indicative" is used herein to refer to the correlation between the identity of the allelic variation(s) in an individual and the susceptibility of an individual to addictive disease, sensitivity to pain and analgesics, therapeutic effectiveness of analgesics, and other physiological manifestations described herein related to the function of the kappa opioid receptor, such as but not limited to the endogenous opioid system, nociception, neurotransmitter release (including dopamine, GABA, noradrenaline, and serotonin), anxiety and stress, learning, memory and cognition, alcohol self-administration, behavioral sensitization to cocaine, drug addiction, opiate withdrawal and tolerance, food intake, immune function, cardiovascular function, renal function, gastrointestinal function, and motor function. Expected correlations of kappa opioid receptor alleles and susceptibility to various conditions may be increased susceptibility or decreased susceptibility.

As explained above, within the scope of the present invention are DNA sequences encoding variant alleles of a human kappa opioid receptor gene of the present invention, which comprise at least one variation in the predominant or "most common" allele of the human kappa opioid receptor gene. The most common allele comprises a DNA sequence of SEQ ID NO:1, and variations in the most common allele comprise G36T, A843G, C846T, C852T, C948T, or C1008T.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, *Cell* 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

The term "corresponding to" is used herein to refer to similar or homologous sequences, whether the exact position is identical or different from the molecule to which the similarity or homology is measured. Thus, the term "corresponding to" refers to the sequence similarity, and not the numbering of the amino acid residues or nucleotide bases.

A variant allele of the human kappa opioid receptor gene of the present invention, whether genomic DNA or cDNA, can be isolated from any source, particularly from a human cDNA or genomic library. Methods for obtaining an allele of a human kappa opioid receptor gene, variants thereof, or the most common, are well known in the art, as described above (see, e.g., Sambrook et al., 1989, supra).

Accordingly, any human cell potentially can serve as the nucleic acid source for the molecular cloning of a variant allele of the human kappa opioid receptor gene of the present invention, or a nucleic acid molecule selectively hybridizable to a variant allele of a human kappa opioid receptor gene of the present invention. The DNA may be obtained by standard procedures known in the art from cloned DNA (e.g., a DNA "library"), and preferably is obtained from a cDNA library prepared from tissues with high level expression of a human kappa opioid receptor protein, by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, an allele of a human kappa opioid receptor gene of the present invention should be molecularly cloned into a suitable vector for propagation.

In the molecular cloning of a human kappa opioid receptor gene of the present invention, DNA fragments are generated, some of which will encode an allele. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing an allele of a human kappa opioid receptor of the present invention may be accomplished in a number of ways. For example, if an amount of a portion of an allele of a human kappa opioid receptor gene, or its specific RNA, or a fragment thereof, is available and can be purified and labeled, the generated DNA fragments may be screened by nucleic acid hybridization to the labeled probe (Benton and Davis, 1977, *Science* 196:180; Grunstein and Hogness, 1975, *Proc. Natl. Acad. Sci. U.S.A.* 72:3961). For example, a set of oligonucleotides corresponding to the partial amino acid sequence information obtained for a human kappa opioid receptor protein can be prepared and used as probes for DNA encoding a variant allele of a human kappa opioid receptor gene of the present invention, as was done in a specific example, infra, or as primers for cDNA or mRNA (e.g., in combination with a poly-T primer for RT-PCR). Preferably, a fragment is selected that is highly unique to a variant allele of the human kappa opioid receptor gene of the invention. Those DNA fragments with substantial homology to the probe will selectively hybridize. As noted above, the greater the degree of homology, the more stringent hybridization conditions can be used.

An allele of a human kappa opioid receptor gene of the present invention can also be identified by mRNA selection, i.e., by nucleic acid hybridization followed by in vitro translation. In this procedure, nucleotide fragments are used to isolate complementary mRNAs by hybridization. Such DNA fragments may represent available, purified DNA of an allele of a human kappa opioid receptor gene of the present invention, or may be synthetic oligonucleotides designed from the partial amino acid sequence information. Immunoprecipitation analysis or functional assays of the in vitro translation products of the products of the isolated mRNAs identifies the mRNA and, therefore, the complementary DNA fragments, that contain the desired sequences.

A labeled cDNA of an allele of a human kappa opioid receptor gene of the present invention, or fragments thereof, or a nucleic acid selectively hybridizable to an allele of a human kappa opioid receptor gene of the present invention, can be synthesized using sequences set forth herein. The radiolabeled mRNA or cDNA may then be used as a probe to identify homologous DNA fragments from among other genomic DNA fragments. Suitable labels include enzymes, radioactive isotopes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker. As noted above, molecular beacons capable of identifying the polymorphisms of the invention are embraced herein.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g., U.V. light to promote fluorescence. Among examples of colored labels, which can be used according to the present invention, include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, supra, Snyder (EP-a 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Other labels for use in the invention include magnetic beads or magnetic resonance imaging labels.

Cloning Vectors

The present invention also relates to cloning vectors comprising variant alleles of a human kappa opioid receptor gene of the present invention, and an origin of replication. For purposes of this Application, an "origin of replication" refers to those DNA sequences that participate in DNA synthesis.

As explained above, in an embodiment of the present invention, variant alleles of a human kappa opioid receptor gene of the present invention comprise a DNA sequence having at least one variation in the most common allele of a human kappa opioid receptor gene comprising a DNA sequence of SEQ ID NO:1, wherein the variation comprises G36T, A843G, C846T, C852T, C948T, or C1008T, or combinations thereof.

Furthermore, an isolated variant allele of a human kappa opioid receptor gene of the present invention, or isolated nucleic acid molecules selectively hybridizable to an isolated variant allele of a human kappa opioid receptor gene of the present invention, can be inserted into an appropriate cloning vector in order to produce multiple copies of the variant allele or isolated nucleic acid molecule. A large number of vector-host systems known in the art may be used. Possible vectors include, but are not limited to, plasmids or modified viruses. The vector system used however must be compatible with the host cell used. Examples of vectors include having applications herein, but are not limited to *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating a variant allele of the human kappa opioid receptor gene of the present invention, or an isolated nucleic acid selectively hybridizable thereto, into a cloning vector which has complementary cohesive termini. However, if the complementary restriction sites used to fragment the variant allele or isolated nucleic acid selectively hybridizable thereto are not present in the cloning vector, the ends of the variant allele or the isolated nucleic acid molecule selectively hybridizable thereto may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Such recombinant molecules can then be introduced into host cells via transformation, transfection, infection, electroporation, etc., so that many copies of a variant allele of a human kappa opioid receptor gene of the present invention, or an isolated nucleic acid molecule selectively hybridizable thereto, can be generated. Preferably, the cloned isolated variant is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2μ plasmid.

In an alternative method an isolated variant allele of a human kappa opioid receptor gene of the present invention or an isolated nucleic acid molecule selectively hybridizable thereto may be identified and isolated after insertion into a suitable cloning vector in a "shot gun" approach. Enrichment for a variant allele, for example, by size fractionation, can be done before insertion into the cloning vector.

Expression Vectors

As stated above, the present invention extends to an isolated variant allele of a human kappa opioid receptor gene, comprising a DNA sequence having at least one variation in the DNA sequence of the predominant or "most common" allele of the human kappa opioid receptor gene comprising a DNA sequence of SEQ ID NO:1 wherein the variations comprise G36T, A843G, C846T, C852T, C948T, or C1008T, or combinations thereof.

Variant alleles of the present invention, along with isolated nucleic acid molecules selectively hybridizable to such variant alleles, can be inserted into an appropriate expression vector, i.e., a vector which contains the necessary elements for the transcription and translation of the inserted protein-coding sequence. Thus, a variant allele of the present invention, or an isolated nucleic acid molecule selectively hybridizable to a variant allele of the present invention, is operatively associated with a promoter in an expression vector of the invention. A DNA sequence is "operatively associated" to an expression control sequence, such as a promoter, when the expression control sequence controls and regulates the transcription and translation of that DNA sequence. The term "operatively associated" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a variant allele of the present invention, or an isolated nucleic acid selectively hybridizable thereto does not contain an appropriate start signal, such a start signal can be inserted into the expression vector in front of (5' of) the molecule.

Both cDNA and genomic sequences can be cloned and expressed under control of such regulatory sequences. An expression vector also preferably includes a replication origin.

The necessary transcriptional and translational signals can be provided on a recombinant expression vector, or they may be supplied by an allele comprising a human kappa opioid receptor gene.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A variant allele of a human kappa opioid receptor gene of the present invention or an isolated nucleic acid molecule selectively hybridizable thereto may be expressed chromosomally, after integration of the coding sequence by recombination. In this regard, any of a number of amplification systems may be used to achieve high levels of stable gene expression (See Sambrook et al., 1989, supra).

A unicellular host transformed or transfected with an expression vector of the present invention is cultured in an appropriate cell culture medium that provides for expression by the unicellular host of the variant allele, or isolated nucleic acid selectively hybridizable thereto.

Any of the methods previously described for the insertion of DNA fragments into a cloning vector may be used to construct expression vectors of the present invention. These methods may include in vitro recombinant DNA and synthetic techniques and in vivo recombination (genetic recombination).

Expression of a variant allele of a human kappa opioid receptor gene of the present invention or an isolated nucleic acid molecule selectively hybridizable to a variant allele of a human kappa opioid receptor gene, may be controlled by any promoter/enhancer element known in the art, but these regulatory elements must be functional in the host selected for expression. Promoters which may be used to control expression include, but are not limited to, the SV40 early promoter region (Benoist and Chambon, 1981, *Nature* 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadal releasing hormone gene control region which is active in the hypothalamus (Mason et al., 1986, Science 234:1372–1378).

Moreover, expression vectors comprising a variant allele of a human kappa opioid receptor gene of the present invention, or an isolated nucleic acid molecule selectively hybridizable thereto, can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the variant allele or isolated nucleic acid molecule selectively hybridizable thereto can be amplified by PCR to provide for detection of the amplified product. This includes a molecular beacon approach to identifying the polymorphisms herein. In the second approach, the presence of a foreign gene inserted into an expression vector of the present invention can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In yet another example, if an isolated variant allele of a human kappa opioid receptor gene of the present invention, or an isolated nucleic acid molecule selectively hybridizable thereto, is inserted within the "selection marker" gene sequence of the vector, recombinants containing the insert can be identified by the absence of the inserted gene function. In the fourth approach, recombinant expression vectors can be identified by assaying for the activity, biochemical, or immunological characteristics of the gene product expressed by the recombinant, provided that the expressed protein assumes a functionally active conformation.

Naturally, the present invention extends to a method of producing a human kappa opioid receptor from the polymorphic variants described herein. Although the variants described herein are "silent," as they do not alter the amino acid sequence of the kappa opioid gene product (i.e., the receptor), the methods herein may be used to determine altered levels of gene expression as a consequence of the presence of one or more of the polymorphisms described herein. An example of such a method comprises the steps of culturing a unicellular host transformed or transfected with an expression vector comprising a variant allele of a human kappa opioid receptor gene comprising a DNA sequence having a variation in SEQ ID NO:1, wherein the variant allele which is operatively associated with a promoter. The transformed or transfected unicellular host is then cultured under conditions that provide for expression of the variant allele of the human kappa opioid receptor gene, and the expression product is recovered from the unicellular host.

Another example involves culturing a unicellular host transformed or transfected with an isolated nucleic acid molecule selectively hybridizable to a variant allele of a human kappa opioid receptor gene comprising a DNA sequence having at least one variation in SEQ ID NO:1, wherein the isolated nucleic acid molecule is operatively associated with a promoter. The variant human kappa opioid receptor is then recovered from the host.

A wide variety of unicellular host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMa1-C2, pET, pGEX (Smith et al., 1988, Gene 67:31–40), pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED PstI, SalI, SbaI, SmaI, and EcoRI cloning site, with the vector expressing both the cloned gene and DHFR; see Kaufman, *Current Protocols in Molecular Biology*, 16.12 (1991).

Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible metallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. *Vaccinia* virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, Acc, HindII, SbaI, BamHI, and Hpa cloning site, TYK or XPRT selection).

Yeast expression systems can also be used according to the invention to produce a variant human kappa opioid receptor or the present invention. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Examples of unicellular hosts contemplated by the present invention include, but are not limited to *E. coli*

Pseudonomas, Bacillus, Streptomyces, yeast, CHO, R1.1, B-W, L-M, COS1, COS7, BSC1, BSC40, BMT10 and Sf9 cells. In addition, a host cell strain may be chosen which modulates the expression of a variant allele comprising a human kappa opioid receptor gene, or an isolated nucleic acid selectively hybridizable thereto, such that the gene product is modified and processed in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, a translocation signal sequence of an isolated variant allele of a human kappa opioid receptor gene of the present invention, or an isolated nucleic acid selectively hybridizable thereto, expressed in bacteria may not be properly spliced. Expression in yeast can produce a glycosylated product. Expression in eukaryotic cells can increase the likelihood of "native" glycosylation and folding. Moreover, expression in mammalian cells can provide a tool for reconstituting, or constituting activity of the variant human kappa opioid receptor gene. Furthermore, different vector/host expression systems may affect processing reactions, such as proteolytic cleavages, to a different extent.

Vectors are introduced into the desired unicellular hosts by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

A Consequently, the present invention extends to a method for determining a susceptibility of a subject to a disease comprising removing a bodily sample comprising a first and second allele of a human kappa opioid receptor gene from the subject, and determining whether either the first or second alleles, or both alleles comprise a DNA sequence having at least one variation in SEQ ID NO:1, wherein the variation comprises G36T, A843G, C846T, C852T, C948T, or C1008T.

Variant alleles of a human kappa opioid receptor gene indicating increased or decrease susceptibility to diseases in the subject as described above, can be detected from cellular sources, such as, but not limited to, whole blood, epithelial cells obtained from the mouth, brain tissue biopsies, adipocytes, testes, heart, and the like. For example, cells can be obtained from an individual by biopsy and lysed, e.g., by freeze-thaw cycling, or treatment with a mild cytolytic detergent such as, but not limited to, TRITON X-100®, digitonin, NONIDET P (NP)-40®, saponin, and the like, or combinations thereof (see, e.g., International Patent Publication WO 92/08981, published May 29, 1992). In yet another embodiment, samples containing both cells and body fluids can be used (see ibid.).

Other methods presently understood by a skilled artisan, and encompassed by the present invention, can also be used to detect the presence of either variation in either or both alleles of a human kappa opioid receptor gene in a sample, and hence increased or decreased susceptibility to at least one disease of the subject relative to the susceptibility of at least one disease in a standard comprising alleles of the human kappa opioid receptor gene comprising a DNA sequence of SEQ ID NO:1.

For example, an optionally detectably labeled isolated nucleic acid molecule selectively hybridizable to an isolated variant allele of a human kappa opioid receptor gene comprising a DNA sequence having a variation in SEQ ID NO:1, wherein the variation comprises G36T, A843G, C846T, C852T, C948T, or C1008T, can be used in standard Northern hybridization analysis to detect the presence, and in some instances quantitate the level of transcription of such a variant allele of the present invention.

Alternatively, oligonucleotides of the invention can be used as PCR primers to amplify an allele of a human kappa opioid receptor gene of the biological sample e.g., by reverse transcriptase-PCR, or amplification of the allele itself. The amplified mRNA or DNA can then be quantified or sequenced in order to determine the presence of a variant allele, and the susceptibility of the subject to addictive diseases. Furthermore, variations in SEQ ID NO:1, as described above, can be found by creation or deletion of restriction fragment length polymorphisms (RFLPs) not found in the predominant or "most common" allele, hybridization with a specific probe engineered to selectively hybridize to variation described, (or lack of hybridization with a probe specific for the predominant or "most common" allele), as well as by other techniques.

Furthermore, biochemical or immunochemical/biochemical (e.g., immunoprecipitation) techniques can be used to detect the presence and or level of expression of a variant allele of a human kappa opioid receptor gene comprising a DNA sequence having a variation in SEQ ID NO:1 as described herein.

Determining Susceptibility to Pain in a Subject

In yet another embodiment, the present invention extends to a method for determining a susceptibility to pain in a subject.

Hence, disclosed herein is a method of determining susceptibility of pain in a subject, comprising the steps of removing a bodily sample comprising a first and second allele of a human kappa opioid receptor gene from the subject, and determining whether either the first or second alleles, or both alleles, comprise a DNA sequence having at least one variation in SEQ ID NO:1, wherein the variation comprises G36T, A843G, C846T, C852T, C948T, or C1008T.

The presence of at least one variation in either or both alleles of the human kappa opioid receptor gene is expected to be indicative of the subject's increased or decreased susceptibility to pain relative to a person homozygous with respect to the predominant or "most common" allele comprising a human kappa opioid receptor gene comprising a DNA sequence of SEQ ID NO:1.

Numerous methods presently available, and understood by the skilled artisan, can be used to "genotype" a subject in regards to the presence of a variant allele of a human kappa opioid receptor gene in the genome of the subject. In particular, methods described above to ascertain increased or decreased susceptibility to addictive diseases have relevance in this embodiment of the present invention, and can readily be used herein. For example, Northern blot hybridization an isolated nucleic acid of the present invention selectively hybridizable to an isolated variant allele of a human kappa opioid receptor gene comprising a DNA sequence having a variation of SEQ ID NO:1, wherein the variation comprises G36T, A843G, C846T, C852T, C948T, or C1008T, as a probe, along with RT-PCR, PCR, and numerous immunoassays described above, have applications herein.

Moreover, once susceptibility to pain in a subject has been determined, it is possible for attending medical professionals treating the subject for pain to administer an appropriate amount of pain reliever to the subject in order to induce analgesia. More specifically, an inappropriate amount of pain reliever is administered to a subject when either the subject is not relieved of pain, or the subject is exposed to potential deleterious side effects of the pain reliever, such as induction of addiction to the pain reliever, brain damage, or death.

However, since the amount of pain reliever administered to a subject is presently based principally on weight, information regarding the genotype of the subject with respect to the human kappa opioid receptor gene can help increase accuracy in determining a therapeutically effective amount of pain reliever to administer in order to induce analgesia, making the use of pain relievers much safer for the subject.

Similarly, once ascertained, a susceptibility to addiction and response to human kappa opioid receptor directed therapeutic agents, appropriate medications and dosages thereof can be determined for treatment of addictive diseases.

Commercial Kits

Furthermore, as explained above, the present invention extends to commercial kits having applications in screening a bodily sample comprising DNA or RNA taken from a subject for the presence of a variant allele comprising a human kappa opioid receptor comprising a DNA sequence having a variation in SEQ ID NO:1, wherein the variation comprises G36T, A843G, C846T, C852T, C948T, or C1008T, or combinations thereof.

With information obtained from the use of a test kit of the present invention, an attending health profession can determine whether the subject has an susceptibility to pain relative to a standard, an increased susceptibility to at least one addictive disease relative to the susceptibility of a standard, a therapeutically effective amount of pain reliever to administer to the subject suffering from pain in order to induce analgesia in the subject relative to the therapeutically effective amount of pain reliever to administer to a standard in order to induce analgesia in the standard, or a therapeutically effective amount therapeutic agent to administer to a subject suffering from at least one addictive disease, relative to the therapeutically effective amount of therapeutic agent to administer to standard suffering from at least one addictive disease. Furthermore, such information can also be used to diagnose a disease or disorder related to a physiological function of the endogenous opioid system, nociception, neurotransmitter release (including dopamine, GABA, noradrenaline, and serotonin), anxiety and stress, learning, memory and cognition, alcohol self-administration, behavioral sensitization to cocaine, drug addition, opiate withdrawal and tolerance, food intake, immune function, cardiovascular function, renal function, gastrointestinal function, and motor function. In each use described above, the standard comprises a first and or second allele of a human kappa opioid receptor gene comprising a DNA sequence of SEQ ID NO:1.

Accordingly, a test kit of the present invention for determining whether a subject comprises a variant allele of a human kappa opioid receptor gene comprising a DNA sequence having a variation in SEQ ID NO:1, comprises means for detecting the presence of a variation in a first and or second allele comprising a human kappa opioid receptor in a biological sample from a subject, and optimally packaged with directions for use of the kit. In one particular aspect, a test kit comprises an oligonucleotide probe(s) for binding to a variant allele of a human kappa opioid receptor gene comprising a DNA sequence having a variation in SEQ ID NO:1; and means for detecting the level of binding of the probe to the variant allele, wherein detection binding of the probe to the variant allele indicates the presence of a variant comprising a human kappa opioid receptor gene comprising a DNA sequence having a variation in SEQ ID NO:1, wherein the variation comprises G36T, A843G, C846T, C852T, C948T, or C1008T, or combinations thereof.

The sequence of the oligonucleotide probe used in a commercial kit will determine which if any variation is present in an allele comprising a human kappa opioid receptor gene. Should no binding be detected, it is probable that no such variation exists in either allele of the subject.

More specifically, a commercial test kit of the present invention comprises:

a) PCR oligonucleotide primers suitable for detection of a variant allele of a human kappa opioid receptor gene comprising a DNA sequence having a variation in SEQ ID NO:1, as set forth above, b) other reagents; and c) directions for use of the kit.

Examples of PCR oligonucleotide primer suitable for detection of an allele comprising a human kappa opioid receptor gene comprising a DNA sequence having a variation in SEQ ID NO:1 can be readily produced by a person of ordinary skill in the art with teaching set forth herein, and variations of SEQ ID NO:1 also set forth herein.

The present invention may be better understood by reference to the following non-limiting Example, which is provided as exemplary of the invention. The following Example is presented in order to more fully illustrate the preferred embodiments of the invention. It should in no way be construed, however, as limiting the broad scope of the invention.

EXAMPLE

To identify polymorphisms of the human kappa opioid receptor, a PCR-based strategy was used to amplify the coding regions of the kappa opioid receptor gene, and to determine the DNA sequence of the amplified exons. Using this method DNA samples were sequenced from 189 unrelated subjects.

Study subjects and procedures. Addictive disease patients, specifically long-term heroin addicts currently in chronic methadone maintenance treatment, and normal control subjects with no history of any drug or alcohol abuse, and individuals with non-opiate drug abuse and dependence were extensively characterized with respect to drug abuse, the addictive diseases, psychological and psychiatric profiles, and medical and ethnic family backgrounds. Unrelated study subjects who were former heroin addicts were referred from methadone treatment clinics in the greater New York City area, primarily those associated with The Biology of Addictive Diseases Laboratory located at The Rockefeller University. These clinics are the Adolescent Development Program and Adult Clinic at the New York Hospital-Cornell Medical Center. Previously heroin-addicted patients admitted to the study conformed to the federally regulated criteria for admission to a methadone maintenance program, that is, one or more years of daily multiple-dose self-administration of heroin or other opiates with the development of tolerance, dependence, and drug-seeking behavior. Current or prior abuse of other drugs was not used as an exclusion criterion for this group as long as opioid abuse continued to be the primary diagnosis.

Unrelated healthy volunteer subjects were recruited primarily through posting of notices and newspaper advertisements or referral by physicians or staff at the Rockefeller University Hospital. Individuals with continuing drug or alcohol abuse or prior extended periods of regular abuse were also studied.

Both addictive disease patients and normal volunteers admitted to the study were assessed by a psychiatrist or research nurse with several psychiatric and psychological instruments as well as the Addiction Severity Index. Study subjects were also administered a detailed personal and medical and special addictive disease questionnaire as well as a family history medical and addictive disease questionnaire designed to provide information regarding substance abuse and major mental illness of first and second degree relatives. Study subjects provided detailed information regarding family origin and ethnic background, including country or geographic area of birth. This information was obtained for both the study subjects themselves and their immediate ancestors (parents, grandparents and great-grandparents), to the extent that the information was known by the study subjects. Study subjects were classified into five groups: African-American, Caucasian, Hispanic (Caribbean and Central or South American origin), Native North American, and Other. The detailed ancestral information collected by the family origin questionnaire allowed classification of study subjects into defined categories. Following psychiatric and behavioral assessment and informed consent and family history acquisition, venipuncture on the study subject was performed, and a blood specimen was taken. Blood samples were processed for DNA extraction and EBV transformation to create stable cell lines that were stored for future studies. All blood samples were coded; the psychiatrists and nurses who performed psychiatric and psychological assessments were blind to the genotypes of the study subjects, and the identity and categorization of the study subjects was unknown to the laboratory research personnel.

By sequencing PCR-amplified DNA from the study subjects, the most common or wild-type allele of the hKOR gene (SEQ ID No:1) was identified, and it was determined that the previously-known GenBank sequence NM_000912, comprised three polymorphic alleles, as compared to the GenBank sequences U17298 and L37362. Based on this limited data, it was not until the present inventors sequenced a large number of hKOR alleles that the most common, or wild-type, allele was confirmable, and the three variations in the NM_000912 identified as polymorphisms and not as suspected sequencing errors. The polymorphisms presently recognized in the NM_000912 sequence were confirmed by finding patients in the present study population with such polymorphisms.

Moreover, three further single-nucleotide polymorphisms were identified among the study subjects. These SNPs were identified in a cohort of 61 (Exon I) and of 189 (Exon III) study subjects. Many of the subjects had multiple variant allelic forms in exon III: six subjects have three SNPs and 19 subjects have two SNPs with different constellations. For SNPs in the predicted mRNA sequence the number +1 is assigned to the first base of the ATG start codon of the receptor. The polymorphisms identified herein are C852T (SEQ ID No:2), present in transmembrane region (TM) VI of exon III; C948T (SEQ ID No:3), present in TM VII of exon III; C1008T (SEQ ID No:4), present in the C-terminal region of exon III; G36T (SEQ ID No:5), present in the N-terminal portion of exon I; A843G (SEQ ID No:6), present in TM VI of exon III; and C846T (SEQ ID No:7), present in TM VI of exon III.

The polymorphisms and number of individuals in which they were identified are as follows:

| Variant | Location | Position | # of individuals | Allelic Freq. of variant SNP |
|---|---|---|---|---|
| G36T | Exon I | N-terminal | n = 61, 14 heterozygous G/T 4 homozygous T/T | 18.0% |
| A843G | Exon III | TM VI | n = 189, 53 heterozygous A/G 22 homozygous G/G | 25.7% |
| C846T | Exon III | TM VI | n = 189, 24 heterozygous, C/T 2 homozygous T/T | 7.4% |
| C852T | Exon III | TM VI | n = 189, 1 heterozygous C/T | <1% |
| C948T | Exon III | TM VII | n = 189, 6 heterozygous C/T | 1.6% |
| C1008T | Exon III | C-terminal | n = 189, 2 heterozygous C/T | <1% |

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. An isolated variant human kappa opioid receptor gene, comprising a DNA sequence consisting of SEQ ID NO:1, with one or more substitutions selected from the group consisting of C852T, C948T, and C1008T, and combinations thereof.

2. The isolated variant of claim 1, detectably labeled.

3. The isolated variant of claim 2, wherein said detectable label comprises a radioactive element, a chemical that fluoresces, or an enzyme.

4. A cloning vector comprising the isolated variant of a human kappa opioid receptor gene of claim 1, and an origin of replication.

5. The cloning vector of claim 4, wherein said cloning vector is selected from the group consisting of a bacteriophages and a plasmid, or derivatives thereof.

6. The cloning vector of claim 5, wherein the bacteriophage is a lambda derivative, and wherein the plasmid is a pBR322 derivative.

7. The cloning vector of claim 5, wherein the plasmid is a pUC plasmid or derivative thereof.

8. The cloning vector of claim 7, wherein the pUC plasmid derivative is selected from the group consisting of pGEX vector, pmal-c, and pFLAG.

9. An expression vector comprising any of the isolated variants of the human kappa opioid receptor gene of claim 1.

10. The expression vector of claim 9, wherein said isolated variant is operatively linked with a promoter selected from the group consisting of immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the trp system, the TAC system, the TRC system, the major operator and promoter regions of phage lambda, control regions of fd coat protein, 3-phosphoglycerate kinase promoter, acid phosphatase promoter, and promoters of yeast α mating factor.

11. An isolated host cell transformed or transfected with an expression vector comprising any of the isolated variants of the human kappa opioid receptor gene of claim 1 operatively associated with a promoter.

12. The isolated host cell of claim 11, wherein said host cell is selected from the group consisting of *E. coli, Pseudomonas, Bacillus, Streptomyces*, yeast, CHO, R1.1, B-W, L-M, COS1, COS7, BSC1, BSC40, BMT10 and Sf9 cells.

* * * * *

SEQUENCE LISTING

<160> NUMBER OF SEQ ID NOS: 7

<210> SEQ ID NO 1
<211> LENGTH: 1154
<212> TYPE: DNA
<213> ORGANISM: homo sapiens

<400> SEQUENCE: 1

```
atggactccc cgatccagat cttccgcggg gagccgggcc ctacctgcgc cccgagcgcc      60
tgcctgcccc ccaacagcag cgcctggttt cccggctggg ccgagcccga cagcaacggc     120
```

| | |
|---|---|
| agcgccggct cggaggacgc gcagctggag cccgcgcaca tctccccggc catcccggtc | 180 |
| atcatcacgg cggtctactc cgtagtgttc gtcgtgggct tggtgggcaa ctcgctggtc | 240 |
| atgttcgtga tcatccgata cacaaagatg aagacagcaa ccaacattta catatttaac | 300 |
| ctggctttgg cagatgcttt agttactaca accatgccct ttcagagtac ggtctacttg | 360 |
| atgaattcct ggccttttgg ggatgtgctg tgcaagatag taatttccat tgattactac | 420 |
| aacatgttca ccagcatctt caccttgacc atgatgagcg tggaccgcta cattgccgtg | 480 |
| tgccaccccg tgaaggcttt ggacttccgc acacccttga aggcaaagat catcaatatc | 540 |
| tgcatctggc tgctgtcgtc atctgttggc atctctgcaa tagtccttgg aggcaccaaa | 600 |
| gtcagggaag acgtcgatgt cattgagtgc tccttgcagt tcccagatga tgactactcc | 660 |
| tggtgggacc tcttcatgaa gatctgcgtc ttcatctttg ccttcgtgat ccctgtcctc | 720 |
| atcatcatcg tctgctacac cctgatgatc ctgcgtctca gagcgtccg gctcctttct | 780 |
| ggctcccgag agaagatcg caacctgcgt aggatcacca actggtcct ggtggtggtg | 840 |
| gcagtcttcg tcgtctgctg gactcccatt cacatattca tcctggtgga ggctctgggg | 900 |
| agcacctccc acagcacagc tgctctctcc agctattact tctgcatcgc cttaggctat | 960 |
| accaacagta gcctgaatcc cattctctac gcctttcttg atgaaaactt caagcggtgt | 1020 |
| ttccgggact tctgctttcc actgaagatg aggatggagc ggcagagcac tagcagagtc | 1080 |
| cgaaatacag ttcaggatcc tgcttacctg agggacatcg atgggatgaa taaaccagta | 1140 |
| tgactagtcg tgga | 1154 |

<210> SEQ ID NO 2
<211> LENGTH: 1154
<212> TYPE: DNA
<213> ORGANISM: homo sapiens

<400> SEQUENCE: 2

| | |
|---|---|
| atggactccc cgatccagat cttccgcggg gagccgggcc ctacctgcgc cccgagcgcc | 60 |
| tgcctgcccc ccaacagcag cgcctggttt cccggctggg ccgagcccga cagcaacggc | 120 |
| agcgccggct cggaggacgc gcagctggag cccgcgcaca tctccccggc catcccggtc | 180 |
| atcatcacgg cggtctactc cgtagtgttc gtcgtgggct tggtgggcaa ctcgctggtc | 240 |
| atgttcgtga tcatccgata cacaaagatg aagacagcaa ccaacattta catatttaac | 300 |
| ctggctttgg cagatgcttt agttactaca accatgccct ttcagagtac ggtctacttg | 360 |
| atgaattcct ggccttttgg ggatgtgctg tgcaagatag taatttccat tgattactac | 420 |
| aacatgttca ccagcatctt caccttgacc atgatgagcg tggaccgcta cattgccgtg | 480 |
| tgccaccccg tgaaggcttt ggacttccgc acacccttga aggcaaagat catcaatatc | 540 |
| tgcatctggc tgctgtcgtc atctgttggc atctctgcaa tagtccttgg aggcaccaaa | 600 |
| gtcagggaag acgtcgatgt cattgagtgc tccttgcagt tcccagatga tgactactcc | 660 |
| tggtgggacc tcttcatgaa gatctgcgtc ttcatctttg ccttcgtgat ccctgtcctc | 720 |
| atcatcatcg tctgctacac cctgatgatc ctgcgtctca gagcgtccg gctcctttct | 780 |
| ggctcccgag agaagatcg caacctgcgt aggatcacca actggtcct ggtggtggtg | 840 |
| gcagtcttcg ttgtctgctg gactcccatt cacatattca tcctggtgga ggctctgggg | 900 |
| agcacctccc acagcacagc tgctctctcc agctattact tctgcatcgc cttaggctat | 960 |
| accaacagta gcctgaatcc cattctctac gcctttcttg atgaaaactt caagcggtgt | 1020 |
| ttccgggact tctgctttcc actgaagatg aggatggagc ggcagagcac tagcagagtc | 1080 |

```
cgaaatacag ttcaggatcc tgcttacctg agggacatcg atgggatgaa taaaccagta    1140
tgactagtcg tgga                                                      1154

<210> SEQ ID NO 3
<211> LENGTH: 1154
<212> TYPE: DNA
<213> ORGANISM: homo sapiens

<400> SEQUENCE: 3
atggactccc cgatccagat cttccgcggg gagccgggcc ctacctgcgc cccgagcgcc      60
tgcctgcccc ccaacagcag cgcctggttt cccggctggg ccgagcccga cagcaacggc     120
agcgccggct cggaggacgc gcagctggag cccgcgcaca tctccccggc catcccggtc     180
atcatcacgg cggtctactc cgtagtgttc gtcgtgggct tggtgggcaa ctcgctggtc     240
atgttcgtga tcatccgata cacaaagatg aagacagcaa ccaacattta catatttaac     300
ctggctttgg cagatgcttt agttactaca accatgccct tcagagtac ggtctacttg      360 atgaattcct ggccttttgg ggatgtgctg tgcaagatag taatttccat tgattactac     420
aacatgttca ccagcatctt caccttgacc atgatgagcg tggaccgcta cattgccgtg     480 tgccacccg tgaaggcttt ggacttccgc acacccttga aggcaaagat catcaatatc      540
tgcatctggc tgctgtcgtc atctgttggc atctctgcaa tagtccttgg aggcaccaaa     600 gtcaggaag acgtcgatgt cattgagtgc tccttgcagt tcccagatga tgactactcc      660
tggtgggacc tcttcatgaa gatctgcgtc ttcatctttg ccttcgtgat ccctgtcctc     720
atcatcatcg tctgctacac cctgatgatc ctgcgtctca agagcgtccg gctccttttct    780 ggctcccgag agaaagatcg caacctgcgt aggatcacca actggtcct ggtggtggtg      840 gcagtcttcg tcgtctgctg gactcccatt cacatattca tcctggtgga ggctctgggg     900
agcacctccc acagcacagc tgctctctcc agctattact tctgcattgc cttaggctat     960
accaacagta gcctgaatcc cattctctac gcctttcttg atgaaaactt caagcggtgt    1020
ttccgggact tctgctttcc actgaagatg aggatggagc ggcagagcac tagcagagtc    1080
cgaaatacag ttcaggatcc tgcttacctg agggacatcg atgggatgaa taaaccagta    1140
tgactagtcg tgga                                                      1154

<210> SEQ ID NO 4
<211> LENGTH: 1154
<212> TYPE: DNA
<213> ORGANISM: homo sapiens

<400> SEQUENCE: 4
atggactccc cgatccagat cttccgcggg gagccgggcc ctacctgcgc cccgagcgcc      60
tgcctgcccc ccaacagcag cgcctggttt cccggctggg ccgagcccga cagcaacggc     120
agcgccggct cggaggacgc gcagctggag cccgcgcaca tctccccggc catcccggtc     180
atcatcacgg cggtctactc cgtagtgttc gtcgtgggct tggtgggcaa ctcgctggtc     240
atgttcgtga tcatccgata cacaaagatg aagacagcaa ccaacattta catatttaac     300
ctggctttgg cagatgcttt agttactaca accatgccct tcagagtac ggtctacttg      360 atgaattcct ggccttttgg ggatgtgctg tgcaagatag taatttccat tgattactac     420
aacatgttca ccagcatctt caccttgacc atgatgagcg tggaccgcta cattgccgtg     480 tgccacccg tgaaggcttt ggacttccgc acacccttga aggcaaagat catcaatatc      540
```

```
tgcatctggc tgctgtcgtc atctgttggc atctctgcaa tagtccttgg aggcaccaaa      600 gtcaggaag acgtcgatgt cattgagtgc tccttgcagt tcccagatga tgactactcc       660
tggtgggacc tcttcatgaa gatctgcgtc ttcatctttg ccttcgtgat ccctgtcctc      720
atcatcatcg tctgctacac cctgatgatc ctgcgtctca agagcgtccg gctcctttct     780
ggctcccgag agaaagatcg caacctgcgt aggatcacca gactggtcct ggtggtggtg     840
gcagtcttcg tcgtctgctg gactcccatt cacatattca tcctggtgga ggctctgggg     900
agcacctccc acagcacagc tgctctctcc agctattact tctgcatcgc cttaggctat     960
accaacagta gcctgaatcc cattctctac gcctttcttg atgaaaattt caagcggtgt     1020
ttccgggact tctgctttcc actgaagatg aggatggagc ggcagagcac tagcagagtc     1080
cgaaatacag ttcaggatcc tgcttacctg agggacatcg atgggatgaa taaaccagta     1140
tgactagtcg tgga                                                        1154
```

<210> SEQ ID NO 5
<211> LENGTH: 1154
<212> TYPE: DNA
<213> ORGANISM: homo sapiens

<400> SEQUENCE: 5

```
atggactccc cgatccagat cttccgcggg gagcctggcc ctacctgcgc cccgagcgcc     60
tgcctgcccc ccaacagcag cgcctggttt cccggctggg ccgagcccga cagcaacggc    120
agcgccggct cggaggacgc gcagctggag cccgcgcaca tctccccggc catcccggtc    180
atcatcacgg cggtctactc cgtagtgttc gtcgtgggct tggtgggcaa ctcgctggtc    240
atgttcgtga tcatccgata cacaaagatg aagacagcaa ccaacattta catatttaac    300
ctggctttgg cagatgcttt agttactaca accatgccct tcagagtac ggtctacttg     360 atgaattcct ggccttttgg ggatgtgctg tgcaagatag taatttccat tgattactac    420
aacatgttca ccagcatctt caccttgacc atgatgagcg tggaccgcta cattgccgtg    480 tgccacccccg tgaaggcttt ggacttccgc acacccttga aggcaaagat catcaatatc    540
tgcatctggc tgctgtcgtc atctgttggc atctctgcaa tagtccttgg aggcaccaaa    600 gtcaggaag acgtcgatgt cattgagtgc tccttgcagt tcccagatga tgactactcc     660
tggtgggacc tcttcatgaa gatctgcgtc ttcatctttg ccttcgtgat ccctgtcctc   720
atcatcatcg tctgctacac cctgatgatc ctgcgtctca agagcgtccg gctcctttct   780
ggctcccgag agaaagatcg caacctgcgt aggatcacca gactggtcct ggtggtggtg   840
gcagtcttcg tcgtctgctg gactcccatt cacatattca tcctggtgga ggctctgggg   900
agcacctccc acagcacagc tgctctctcc agctattact tctgcatcgc cttaggctat   960
accaacagta gcctgaatcc cattctctac gcctttcttg atgaaaactt caagcggtgt    1020
ttccgggact tctgctttcc actgaagatg aggatggagc ggcagagcac tagcagagtc    1080
cgaaatacag ttcaggatcc tgcttacctg agggacatcg atgggatgaa taaaccagta    1140
tgactagtcg tgga                                                      1154
```

<210> SEQ ID NO 6
<211> LENGTH: 1154
<212> TYPE: DNA
<213> ORGANISM: homo sapiens

<400> SEQUENCE: 6

```
atggactccc cgatccagat cttccgcggg gagccgggcc ctacctgcgc cccgagcgcc     60
```

```
tgcctgcccc caacagcag cgcctggttt cccggctggg ccgagcccga cagcaacggc      120
agcgccggct cggaggacgc gcagctggag cccgcgcaca tctccccggc catcccggtc      180
atcatcacgg cggtctactc cgtagtgttc gtcgtgggct tggtgggcaa ctcgctggtc      240
atgttcgtga tcatccgata cacaaagatg aagacagcaa ccaacattta catatttaac      300
ctggctttgg cagatgcttt agttactaca accatgccct ttcagagtac ggtctacttg      360
atgaattcct ggccttttgg ggatgtgctg tgcaagatag taatttccat tgattactac      420
aacatgttca ccagcatctt caccttgacc atgatgagcg tggaccgcta cattgccgtg      480 tgccacccg tgaaggcttt ggacttccgc acacccttga aggcaaagat catcaatatc      540
tgcatctggc tgctgtcgtc atctgttggc atctctgcaa tagtccttgg aggcaccaaa      600
gtcagggaag acgtcgatgt cattgagtgc tccttgcagt tcccagatga tgactactcc      660
tggtgggacc tcttcatgaa gatctgcgtc ttcatctttg ccttcgtgat ccctgtcctc      720
atcatcatcg tctgctacac cctgatgatc ctgcgtctca agagcgtccg gctcctttct      780
ggctcccgag agaaagatcg caacctgcgt aggatcacca gactggtcct ggtggtggtg      840
gcggtcttcg tcgtctgctg gactcccatt cacatattca tcctggtgga ggctctgggg      900
agcacctccc acagcacagc tgctctctcc agctattact tctgcatcgc cttaggctat      960
accaacagta gcctgaatcc cattctctac gcctttcttg atgaaaactt caagcggtgt      1020
ttccgggact tctgctttcc actgaagatg aggatggagc ggcagagcac tagcagagtc      1080
cgaaatacag ttcaggatcc tgcttacctg agggacatcg atgggatgaa taaaccagta      1140
tgactagtcg tgga                                                         1154

<210> SEQ ID NO 7
<211> LENGTH: 1154
<212> TYPE: DNA
<213> ORGANISM: homo sapiens

<400> SEQUENCE: 7
atggactccc cgatccagat cttccgcggg gagccgggcc ctacctgcgc cccgagcgcc      60
tgcctgcccc caacagcag cgcctggttt cccggctggg ccgagcccga cagcaacggc     120
agcgccggct cggaggacgc gcagctggag cccgcgcaca tctccccggc catcccggtc     180
atcatcacgg cggtctactc cgtagtgttc gtcgtgggct tggtgggcaa ctcgctggtc     240
atgttcgtga tcatccgata cacaaagatg aagacagcaa ccaacattta catatttaac     300
ctggctttgg cagatgcttt agttactaca accatgccct ttcagagtac ggtctacttg     360
atgaattcct ggccttttgg ggatgtgctg tgcaagatag taatttccat tgattactac     420
aacatgttca ccagcatctt caccttgacc atgatgagcg tggaccgcta cattgccgtg     480 tgccacccg tgaaggcttt ggacttccgc acacccttga aggcaaagat catcaatatc     540
tgcatctggc tgctgtcgtc atctgttggc atctctgcaa tagtccttgg aggcaccaaa     600
gtcagggaag acgtcgatgt cattgagtgc tccttgcagt tcccagatga tgactactcc     660
tggtgggacc tcttcatgaa gatctgcgtc ttcatctttg ccttcgtgat ccctgtcctc     720
atcatcatcg tctgctacac cctgatgatc ctgcgtctca agagcgtccg gctcctttct     780
ggctcccgag agaaagatcg caacctgcgt aggatcacca gactggtcct ggtggtggtg     840
gcagttttcg tcgtctgctg gactcccatt cacatattca tcctggtgga ggctctgggg     900
agcacctccc acagcacagc tgctctctcc agctattact tctgcatcgc cttaggctat     960
```

```
accaacagta gcctgaatcc cattctctac gcctttcttg atgaaaactt caagcggtgt    1020
ttccgggact tctgctttcc actgaagatg aggatggagc ggcagagcac tagcagagtc    1080
cgaaatacag ttcaggatcc tgcttacctg agggacatcg atgggatgaa taaaccagta    1140
tgactagtcg tgga                                                      1154
```